US010267718B2

(12) United States Patent
Johnson (10) Patent No.: US 10,267,718 B2
(45) Date of Patent: Apr. 23, 2019

(54) ADDITIVE MANUFACTURED COMPONENT THAT INDICATES WEAR AND SYSTEM AND METHOD THEREOF

(71) Applicant: Caterpillar Inc., Peoria, IL (US)

(72) Inventor: Lonny E. Johnson, Peoria, IL (US)

(73) Assignee: Caterpillar Inc., Deerfield, IL (US)

( * ) Notice: Subject to any disclaimer, the term of this patent is extended or adjusted under 35 U.S.C. 154(b) by 166 days.

(21) Appl. No.: 15/088,738

(22) Filed: Apr. 1, 2016

(65) Prior Publication Data

US 2017/0284914 A1  Oct. 5, 2017

(51) Int. Cl.
| | |
|---|---|
| *G01N 3/56* | (2006.01) |
| *G01M 99/00* | (2011.01) |
| *F16H 55/06* | (2006.01) |
| *G01M 13/022* | (2019.01) |
| *F27D 1/16* | (2006.01) |
| *F27D 21/00* | (2006.01) |
| *C21B 7/04* | (2006.01) |

(52) U.S. Cl.
CPC ............... *G01N 3/56* (2013.01); *F16H 55/06* (2013.01); *G01M 13/022* (2013.01); *G01M 99/00* (2013.01); *C21B 7/04* (2013.01); *F16H 2055/065* (2013.01); *F27D 1/1621* (2013.01); *F27D 21/0021* (2013.01); *G01N 2203/0664* (2013.01)

(58) Field of Classification Search
CPC ....... F27D 1/1621; F27D 1/0021; C21B 7/04; G01N 3/56; G01N 2203/0664; G01M 99/00; B22F 3/1055; B29C 64/00

USPC .......... 116/200–201, 204, 208–209; 73/431, 73/762, 866.5; 702/185
See application file for complete search history.

(56) References Cited

U.S. PATENT DOCUMENTS

| | | | | | |
|---|---|---|---|---|---|
| 3,678,883 | A | * | 7/1972 | Fischer | B23Q 17/09 116/208 |
| 4,620,185 | A | * | 10/1986 | Plahmer | F16N 29/00 324/71.1 |
| 5,348,515 | A | * | 9/1994 | Miller | B62D 55/12 474/152 |
| 5,451,110 | A | * | 9/1995 | Gams, Jr. | B02C 2/06 116/208 |
| 5,796,349 | A | * | 8/1998 | Klein | F16C 17/04 116/208 |
| 6,415,735 | B1 | * | 7/2002 | Rogers | F16D 3/185 116/208 |

(Continued)

*Primary Examiner* — R. A. Smith
*Assistant Examiner* — Tania Courson
(74) *Attorney, Agent, or Firm* — Oblon, McClelland, Maier & Neustadt (57) ABSTRACT

A three-dimensional printed metal component for a lubricated system is provided. The metal component includes a three-dimensional printed metal body formed of a plurality of metal layers of a first metal and having a contact surface configured to movingly contact another component of the lubricated system. The metal component further includes at least one first three-dimensional printed wear-identifying layer of a material different from the first metal embedded in the metal body at a predetermined depth, a predetermined distance from an outer surface portion of the contact surface. The predetermined distance defines a predetermined wear state of the contact surface associated with replacement of the metal component.

16 Claims, 10 Drawing Sheets

(56) References Cited

U.S. PATENT DOCUMENTS

| | | | | |
|---|---|---|---|---|
| 6,600,965 B1* | 7/2003 | Hull | | G01J 1/4257 156/273.3 |
| 6,672,245 B2* | 1/2004 | Ford | | A61H 3/0288 116/208 |
| 6,786,153 B2* | 9/2004 | Burrow | | B41F 31/027 101/153 |
| 6,846,261 B2* | 1/2005 | Lev | | F16H 55/06 29/893.1 |
| 6,854,194 B2* | 2/2005 | Hansen | | G01M 1/045 116/208 |
| 7,018,313 B2* | 3/2006 | Nakamura | | F16H 55/30 474/152 |
| 7,455,740 B2* | 11/2008 | Bostanjoglo | | B22F 3/1055 148/525 |
| 7,604,768 B2* | 10/2009 | Kritchman | | B29C 64/245 264/401 |
| 8,131,509 B2* | 3/2012 | Novis | | G05B 23/0229 702/185 |
| 8,171,637 B2* | 5/2012 | Michaud | | F16H 55/06 216/52 |
| 8,343,437 B2* | 1/2013 | Patel | | G01D 3/10 422/424 |
| 8,695,445 B2* | 4/2014 | Laurer | | F01D 5/12 116/208 |
| 9,157,832 B2* | 10/2015 | Uluyol | | G01M 13/045 |
| 9,307,827 B2* | 4/2016 | Brewer | | A46B 15/001 |
| 9,670,782 B2* | 6/2017 | Gohler; Jens | | F01D 5/286 |
| 9,920,646 B2* | 3/2018 | Lee | | F01D 11/122 |
| 9,931,697 B2* | 4/2018 | Levin | | B29C 64/40 |
| 2001/0008317 A1* | 7/2001 | Gaylo | | A61K 31/192 264/86 |
| 2002/0000041 A1* | 1/2002 | Doroodian-Shoja | | B26B 21/4087 30/41.7 |
| 2006/0037222 A1* | 2/2006 | Hunt | | G06K 19/06009 40/326 |
| 2007/0175381 A1* | 8/2007 | Harder | | F16D 67/02 116/208 |
| 2007/0252115 A1* | 11/2007 | Arehart | | A41D 19/0082 252/583 |
| 2009/0211421 A1* | 8/2009 | Lier | | B23D 61/026 83/522.27 |
| 2011/0135840 A1* | 6/2011 | Doye | | B22F 3/1055 427/554 |
| 2011/0138951 A1* | 6/2011 | Mashue | | F16H 55/17 74/457 |
| 2011/0307218 A1* | 12/2011 | Kar | | G05B 23/0221 702/185 |
| 2013/0331949 A1* | 12/2013 | Dehoff | | A61F 2/583 623/26 |
| 2014/0102791 A1* | 4/2014 | Dupont | | E21B 12/02 175/39 |
| 2015/0060042 A1* | 3/2015 | Shilpiekandula | | B22F 3/008 166/65.1 |
| 2016/0084746 A1* | 3/2016 | Klikovich | | G01N 3/56 116/208 |
| 2017/0036403 A1* | 2/2017 | Ruff | | B33Y 30/00 |
| 2017/0136703 A1* | 5/2017 | Hayes | | B33Y 50/00 |
| 2017/0252471 A1* | 9/2017 | Patel | | G01K 3/04 |
| 2017/0288870 A1* | 10/2017 | Przydatek | | H04L 63/06 |
| 2017/0321793 A1* | 11/2017 | Wu | | B32B 37/1018 |
| 2017/0356165 A1* | 12/2017 | Serrurier | | G06F 17/50 |
| 2018/0185955 A1* | 7/2018 | Hsu | | B23K 20/10 |
| 2018/0313442 A1* | 11/2018 | Ning | | F16H 55/14 |

\* cited by examiner

FIG. 10 even though the component has remaining service life. Such premature replacement of a component otherwise within operational tolerances can affect economical and out-of-service aspects associated with operation of the machine. In either of the foregoing cases, replacing the component on the basis of the expected service life, despite the actual wear condition of the component, may lead to economical loss, unnecessary downtime, maintenance inconvenience, and ineffective machine operation.

ADDITIVE MANUFACTURED COMPONENT THAT INDICATES WEAR AND SYSTEM AND METHOD THEREOF

TECHNICAL FIELD

The present disclosure relates to detection of wear in a component, and more particularly to an additive manufactured component that indicates wear and a system and a method to indicate wear of the additive manufactured component.

BACKGROUND

Moving components of a machine tend to wear out over time. A variety of factors, such as aging, extended duration operations, load conditions, improper maintenance, and improper handling of the machine may contribute to wear of moving components to a point of an out-of-tolerance condition or even failure. It is relevant to ensure that such components are timely replaced in order to avoid or minimize damage to the machine. Usually, such components are provided with an expected service life based, for instance, in an expected use or application and prior empirical wear data. For example, a component may be manufactured with an expected service life of 400 hours. Therefore, it is recommended or required that the component be replaced only upon 400 hours of operations in order to eliminate or reduce the possibility of damage to the machine caused by excessive wear of the component.

However, due to dynamic working conditions of the machine, a component may wear out before the completion of the expected service life, e.g., due to overloading of the component. In such a case, using a component that has met or exceeded its wear tolerances may result in faults in the machine, which may, in turn, affect operation of the machine. On the other hand, in certain circumstances, a component may wear at a slow rate than expected, e.g., due to under-loading. However, since the component, according to its predetermined service life, is due for replacement, the component may be replaced anyway, even though the component has remaining service life. Such premature replacement of a component otherwise within operational tolerances can affect economical and out-of-service aspects associated with operation of the machine. In either of the foregoing cases, replacing the component on the basis of the expected service life, despite the actual wear condition of the component, may lead to economical loss, unnecessary downtime, maintenance inconvenience, and ineffective machine operation.

SUMMARY OF THE DISCLOSURE

In one aspect of the present disclosure, a three-dimensional printed metal gear component for an enclosed oil system is provided. The three-dimensional printed metal gear component includes a three-dimensional printed metal body formed of a plurality of metal layers of a first metal and having a plurality of teeth. The three-dimensional printed metal gear component further includes at least one first three-dimensional printed wear-identifying layer of a second metal, different from the first metal, embedded in at least one tooth of the plurality of teeth, at a first predetermined depth from a first outer surface portion of the at least one tooth. All sides of the at least one first three-dimensional printed wear-identifying layer are surrounded by the metal body. The first outer surface portion of the at least one tooth is constructed to movingly contact a second metal gear component of the enclosed oil system different from the three-dimensional printed metal gear component. The first predetermined depth defines a predetermined wear state of the at least one tooth associated with replacement of the three-dimensional printed metal gear component.

In another aspect of the present disclosure, a system is provided and includes a first three-dimensional printed metal part for a first lubricated sub-system. The first three-dimensional printed metal part includes a first three-dimensional printed metal body formed of a plurality of metal layers of a first metal and having a plurality of contact surfaces. The first three-dimensional printed metal part further includes at least one first three-dimensional printed marker layer of a first material different from the first metal. The at least one first three-dimensional printed marker layer is positioned in the first three-dimensional printed metal body at a first predetermined depth from a first contact surface of the plurality of contact surfaces. The first predetermined depth is indicative of an amount of wear of the first contact surface associated with replacement of the first three-dimensional printed metal part.

In yet another aspect of the present disclosure, a method is provided and includes additive printing a plurality of metal layers of a first metal to form a first printed metal body having a first contact surface, and additive printing at least one first wear marker layer of a second metal, different from the first metal. The at least one first wear marker layer is provided in the first printed metal body at a first predetermined distance away from the first contact surface. The first predetermined distance is indicative of an amount of wear of the first contact surface associated with replacement of the first printed metal body.

Other features and aspects of this disclosure will be apparent from the following description and the accompanying drawings.

BRIEF DESCRIPTION OF THE DRAWINGS

The accompanying drawings, which are incorporated in and constitute a part of the specification, are illustrative of one or more embodiments and, together with the description, explain the embodiments. The accompanying drawings have not necessarily been drawn to scale. Further, any values or dimensions in the accompanying drawings are for illustration purposes only and may or may not represent actual or preferred values or dimensions. Where applicable, some or all select features may not be illustrated to assist in the description and understanding of underlying features.

DETAILED DESCRIPTION

The description set forth below in connection with the appended drawings is intended as a description of various embodiments of the described subject matter and is not necessarily intended to represent the only embodiment(s). In certain instances, the description includes specific details for the purpose of providing an understanding of the described subject matter. However, it will be apparent to those skilled in the art that embodiments may be practiced without these specific details. In some instances, well-known structures and components may be shown in block diagram form in order to avoid obscuring the concepts of the described subject matter. Wherever possible, corresponding or similar reference numbers will be used throughout the drawings to refer to the same or corresponding parts.

Any reference in the specification to "one embodiment" or "an embodiment" means that a particular feature, structure, characteristic, operation, or function described in connection with an embodiment is included in at least one embodiment. Thus, any appearance of the phrases "in one embodiment" or "in an embodiment" in the specification is not necessarily referring to the same embodiment. Further, the particular features, structures, characteristics, operations, or functions may be combined in any suitable manner in one or more embodiments, and it is intended that embodiments of the described subject matter can and do cover modifications and variations of the described embodiments.

It must also be noted that, as used in the specification, appended claims and abstract, the singular forms "a," "an," and "the" include plural referents unless the context clearly dictates otherwise. That is, unless clearly specified otherwise, as used herein the words "a" and "an" and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit embodiments of the described subject matter to any particular orientation or configuration. Furthermore, terms such as "first," "second," "third," etc. merely identify one of a number of portions, components, points of reference, operations or functions as described herein, and likewise do not necessarily limit embodiments of the described subject matter to any particular configuration, orientation, or sequence of functions or operations.

Generally speaking, the present disclosure involves an additive manufactured component, and systems and method thereof, that includes one or more additive manufactured wear-indicating portions at pre-set locations in the additive manufactured component. The location of each pre-set wear-indicating portion is associated with a wear state of the additive manufactured component. Further, wear particles from the wear-indicating portions resulting from component wear may be sensed, onboard and/or off-board a corresponding piece of machinery, to identify the wear state of the additive manufactured component. Further, in general, embodiments of the present disclosure involve parts that have one or more lubricated metal on metal contact points or areas, such as a gear, a rotating shaft, a cam follower, a valve overhead rocker, one or more components of a piston-to-connecting rod interface (including a pin connecting the piston and rod), one or more components of a connecting rod-to-crank interface (including a bearing between the rod and crank), one or more components of a crank-to-block interface (including a bearing between the connecting rod and crank), and one or more components of an engine turbocharger, such as a turbo shaft or a bushing or a bearing between the turbo shaft and housing of the turbocharger.

Figure 1:
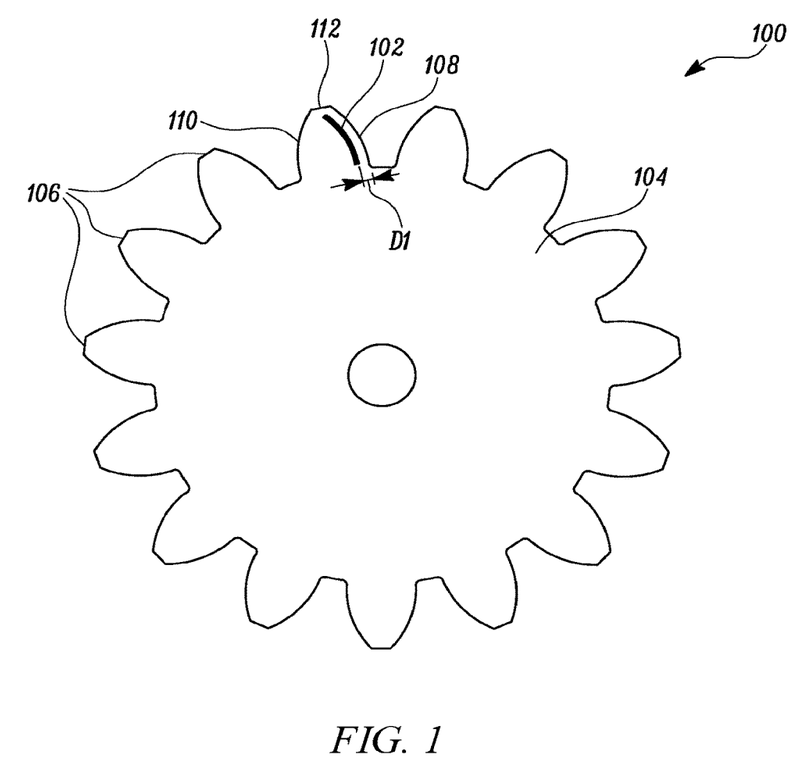
FIG. 1 is a diagrammatic cross-sectional view of a component with wear-identifying material, according to one or more embodiments of the present disclosure.
Figure 7:
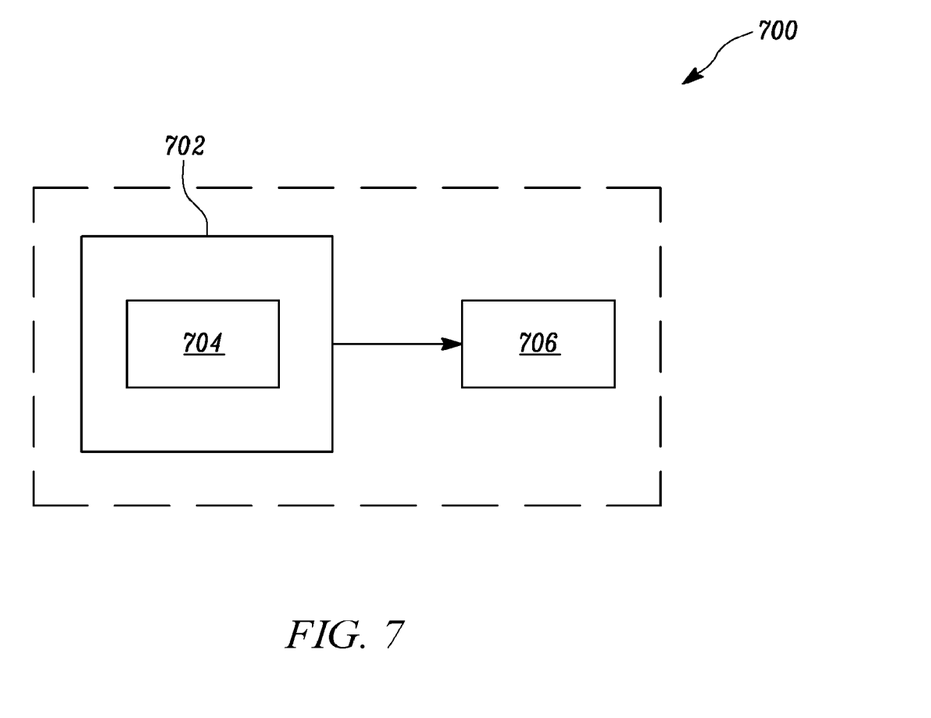
FIG. 7 is a block diagram of a system with a lubricated sub-system, according to one or more embodiments of the present disclosure.
Figure 8:
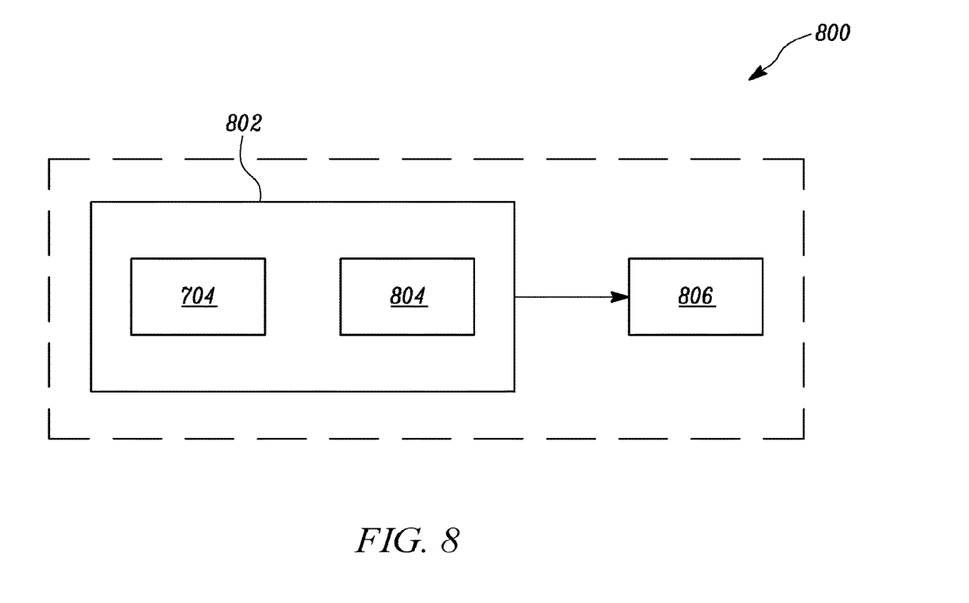
FIG. 8 is a block diagram of a system with a lubricated sub-system, according to one or more embodiments of the present disclosure.
Figure 9:
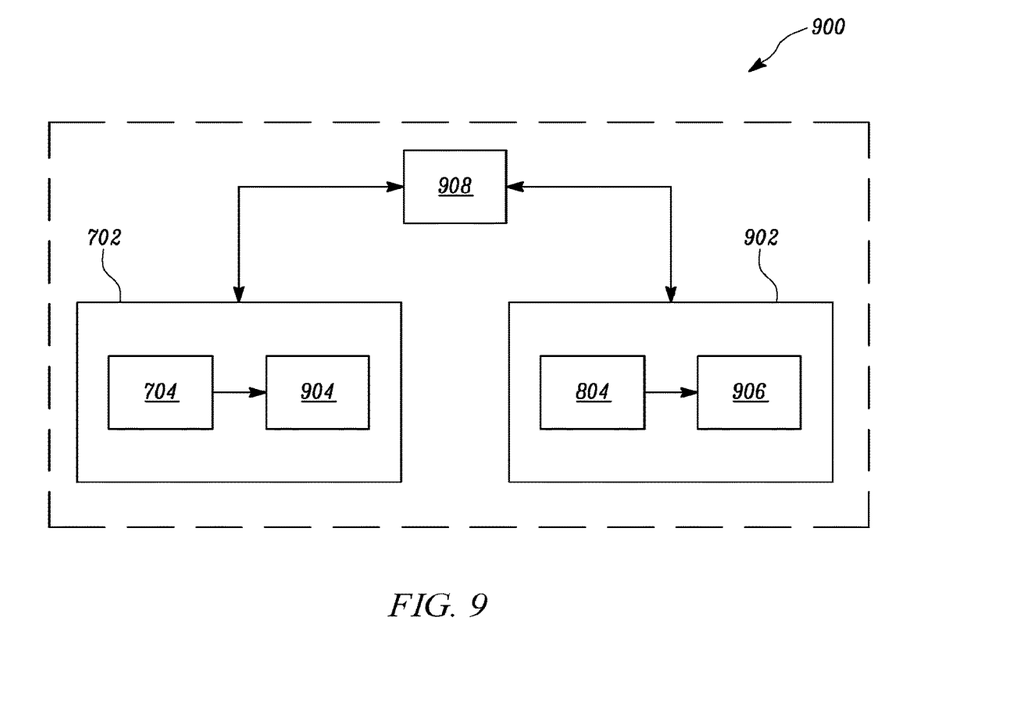
FIG. 9 is a block diagram of a system with a first lubricated sub-system and a second lubricated sub-system, according to one or more embodiments of the present disclosure.

FIG. 1 illustrates a diagrammatic cross-sectional view of a component 100 with wear-identifying material 102, according to one or more embodiments of the present disclosure. The component 100 may include, but is not limited to, a pinion, a rack, a bushing, a gear, and a shaft of a lubricated system, such as an enclosed oil system (e.g., as shown in FIGS. 7, 8, 9). The enclosed oil system may include, but is not limited to, an engine oil system, a transmission oil system, a pump, and a drive system of any machine.

The component 100 associated with FIG. 1 is a three-dimensional printed metal gear component, hereinafter referred to as metal gear component 100. However, although the present disclosure is explained with regard to metal gear component 100, it should be noted that the scope of the present disclosure is not limited to the metal gear component 100, and may include other components as explained herein.

The metal gear component 100 may be manufactured using any suitable additive manufacturing technique, such as a 3-Dimensional (3-D) printing technique. For manufacturing the metal gear component 100 using a 3-D printing technique, a 3-D Computer-Aided Design (CAD) of the metal gear component 100 may be modeled. Further, the 3-D CAD model may be processed by a slicing technique to convert the 3-D CAD model into thin layers. Following the conversion, the 3-D CAD model may be fed to a 3-D printing machine. The 3-D printing machine may include a printing module that operates based on spatial coordinates created by the 3-D CAD model. Subsequently, the 3-D printing machine manufactures the metal gear component 100 by depositing layers of metal one over another, including different metal layers or metal layers and non-metal layers, as will be discussed in more detail below. For example, the metal gear component 100 may be "built up" in layers in a direction of its central axis. In one or more embodiments, the metal gear component 100, after being printed, may be heat treated, coated with another metal, for example, with a zinc plating layer, and then installed in an enclosed oil system, for instance.

Although, the present embodiment explains the manufacturing of the metal gear component 100 using a 3-D printing technique, the metal gear component 100 may be manufactured by other additive manufacturing techniques without departing from the scope of the present disclosure. Such additive manufacturing techniques may include, but are not limited to, powder manufacturing techniques and metal deposition techniques.

The metal gear component 100 includes a three-dimensional printed metal body 104, hereinafter referred to as metal body 104, and a three-dimensionally printed wear-identifying material 102 in the metal body 104. All sides of the wear identifying material 102 may be surrounded by the metal body 104. Alternatively, the wear-identifying material 102 may be exposed at opposite sides of the metal body 104.

The metal body 104 may be formed of a plurality of metal layers of a first metal. The first metal may include, but is not limited to, aluminum, cast iron, steel, brass, and copper. The first metal for manufacturing the metal body 104 may be selected based on one or more of application, dimensional characteristics, and functional characteristics of the metal gear component 100 and/or type of additive manufacturing machine or process.

According to FIG. 1, the metal body 104 includes a plurality of teeth 106. Each of the teeth 106 includes a first outer surface portion 108, a second outer surface portion 110, and a top surface portion 112. Each tooth 106 may engage with or movingly contact another metal gear component (not shown in FIG. 1), for example, in a rack-and-pinion arrangement, through at least the first outer surface portion 108 and the second outer surface portion 110.

Further, the wear-identifying material 102 may be embedded in the metal body 104 in layers. That is, the wear-identifying material 102 may be embedded in the metal body in the form of at least one three-dimensional printed wear-identifying layer, hereinafter referred to as wear-identifying layer 102. To be clear, the wear-identifying layer 102 may be a plurality of successive layers of wear-identifying material, for instance, formed using additive manufacturing.

The wear-identifying layer 102 can be embedded in at least one tooth 106, from among the plurality of teeth 106, at a first predetermined depth 'D1' from the first outer surface portion 108 of the one tooth 106. The wear-identifying layer 102 may be embedded in such a manner that the first wear-identifying layer 102 is surrounded by the metal body 104, completely or partially (e.g., the sides of the wear-identifying layer may be exposed from respective sides of the metal body 104). Therefore, the wear-identifying layer 102 may or may not be exposed to the atmosphere when embedded in the metal body 104.

The first predetermined depth D1 may define a predetermined wear state of the tooth 106. For example, the first predetermined depth D1 may be defined based on a load or expected load of the metal gear component 100 and corresponding wear rate. The load of the metal gear component 100 may depend on various factors, such as operational characteristics, number of working hours, and environmental factors associated with the metal gear component 100.

Additionally or alternatively, the first predetermined depth D1 may be defined based on a wear rate of the metal gear component 100 and user wear notification requirements. For example, if the user wishes to be notified at a service half-life of the metal gear component 100, the first predetermined depth D1 may be defined to indicate the service half-life of the metal gear component 100. Similarly, if the user wishes to be notified of a requirement or need to replace the metal gear component 100, the first predetermined depth D1 may be defined to indicate the full service life of the metal gear component 100. Therefore, the first predetermined depth D1 at which the first wear-identifying layer 102 is to be embedded or disposed in the metal body 104 may vary based on at least one of the expected load to be experienced by the metal gear component 100 and the wear rate of the metal gear component 100. Additionally, the first predetermined depth D1 may be located based on desired information to be obtained, such as when the metal gear component 100 reaches its half-life or full-life, or a rate of wear from a particular wear point to another.

The predetermined wear state can be indicative of a wear amount of the first outer surface portion 108 of the tooth 106. Wear of the metal body 104 to the first wear-identifying layer 102 may indicate that the predetermined wear state of the tooth 106 or the metal gear component 100 is achieved. The predetermined wear state may be associated with replacement of the metal gear component 100, either immediate or anticipated. In one or more embodiments, the predetermined wear state may be indicative of an out-of-tolerance condition or a failure condition of the tooth 106 or the metal gear component 100. Additionally or alternatively, the predetermined wear state may be indicative of an expected out-of-tolerance condition or an expected failure condition of the tooth 106 or the metal gear component 100. In yet another embodiment, the predetermined wear state may be indicative of a half-life of the tooth 106 or the metal gear component 100.

Furthermore, the first wear-identifying layer 102 may be formed of a material different from the first metal of the metal body 104, for instance, a second metal different from the first metal. The second metal may include, but is not limited to, bronze, chrome, titanium, or a combination of two or more thereof. In one example, titanium can be used as the second metal when the enclosed oil system belongs to an aircraft. As another example, the first wear-identifying layer 102 may be formed of a relatively hard non-metal, e.g., carbon fibers.

The material of the first wear-identifying layer 102 may be different from any material used in an oil system in which the metal gear component 100 is arranged or intended to be arranged. That is, the material of the first wear-identifying layer 102 can be a material not found or not normally found in an oil system, such as an enclosed oil system, which can be more readily detected as a foreign substance to the enclosed oil system and thus indicative of a pre-set amount of wear of the metal gear component 100. Materials used in an oil system according to one or more embodiments of the disclosed subject matter may include iron, copper, tin, aluminum, lead, silicon, silver, steel, and metal additives, such as boron, magnesium, calcium, molybdenum, barium, and phosphorus. Therefore, the material of the first wear-identifying layer 102 may be different from the aforementioned materials of the oil system.

In case of wear of the metal gear component 100, particularly of the first outer surface 108 to the first wear-identifying layer 102, portions of the first wear-identifying layer 102 may detach due to wear and can be detectable in an oil sample analysis. Generally speaking, oil sample analysis is a technique to determine lubricant properties, impurities, and wear debris, which can be indicative of a working condition of a machine having the oil system. The oil sample analysis may include, but is not limited to, an Inductively Coupled Plasma (ICP) spectroscopy, a Particle Quantification Index (PQI) test, a viscosity test, and a water test.

When wear of the tooth 106 or the metal gear component 100 occurs, the first wear-identifying layer 102 may become exposed to the lubricant or the oil present within the oil system. Further wear of the first wear-identifying layer 102 can result in particles of the first wear-identifying layer 102 being introduced to the lubricant, as noted above. Such particles of the first wear-identifying layer 102 may be detected in an oil sample analysis, which can indicate the metal gear component 100 or portion thereof has achieved a particular wear state or condition.

The oil sample analysis may be performed on-board the machine carrying the enclosed oil system, for instance, using one or more sensors or sensing circuitry to detect existence of particles of the first wear-identifying layer 102. In another embodiment, the oil sample analysis may be performed off-board the machine, with a sample of oil being pulled from the oil system.

Figure 2:
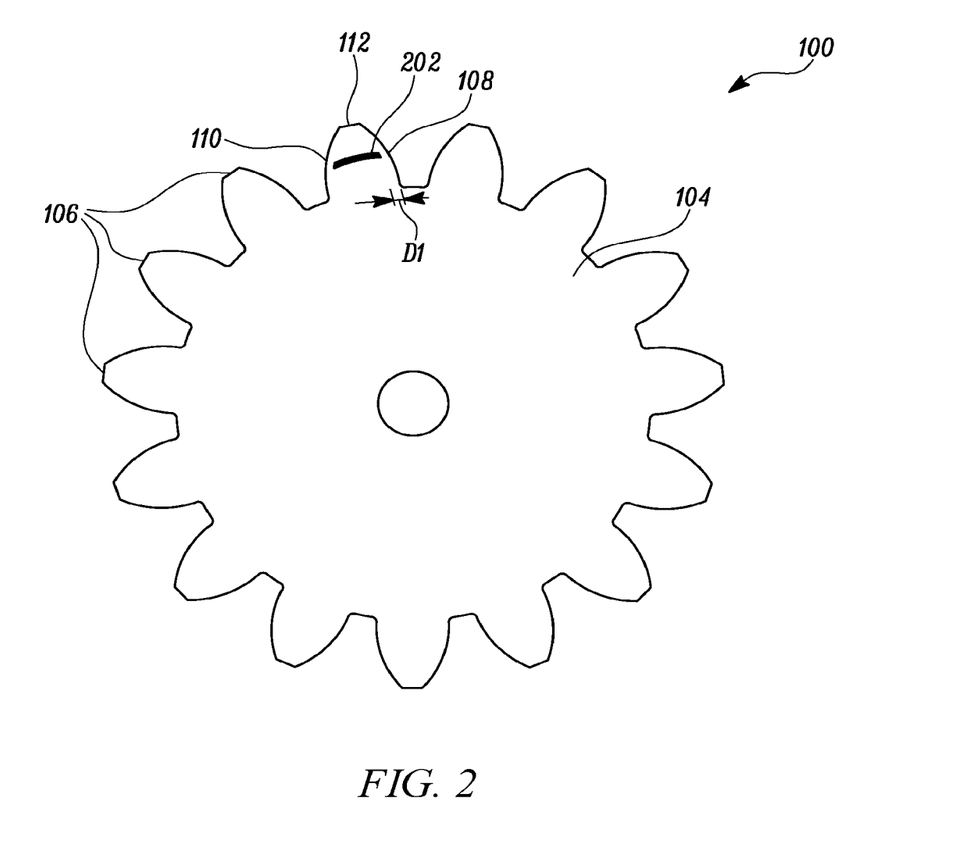
FIG. 2 is a diagrammatic cross-sectional view of a component with wear-identifying material, according to one or more embodiments of the present disclosure.

FIG. 2 illustrates a diagrammatic cross-sectional view of the metal gear component 100 with a wear-identifying layer 202, according to one or more embodiments of the present disclosure. As shown, the positioning of the wear-identifying layer 202 within the metal body 104 is changed with respect to as illustrated in FIG. 1. In particular, the wear-identifying layer 202 can be disposed substantially parallel to the top surface portion 112 of the tooth 106 at a first predetermined depth D1 from the first outer surface portion 108. Such positioning of the first wear-identifying layer 202 may assist in detecting wear of the metal gear component 100 through the first outer surface portion 108 as well as through the second outer surface portion 110, for instance, without having to create distinct wear-identifying portions as the wear-identifying layer 202 is built up in successive layers (i.e., in a direction out of the page with reference to FIG. 2) in an additive manufacturing process. The characteristics of the wear-identifying layer 202 may be the same as explained for the first wear-identifying layer 102 described in relation to FIG. 1.

Figure 3:
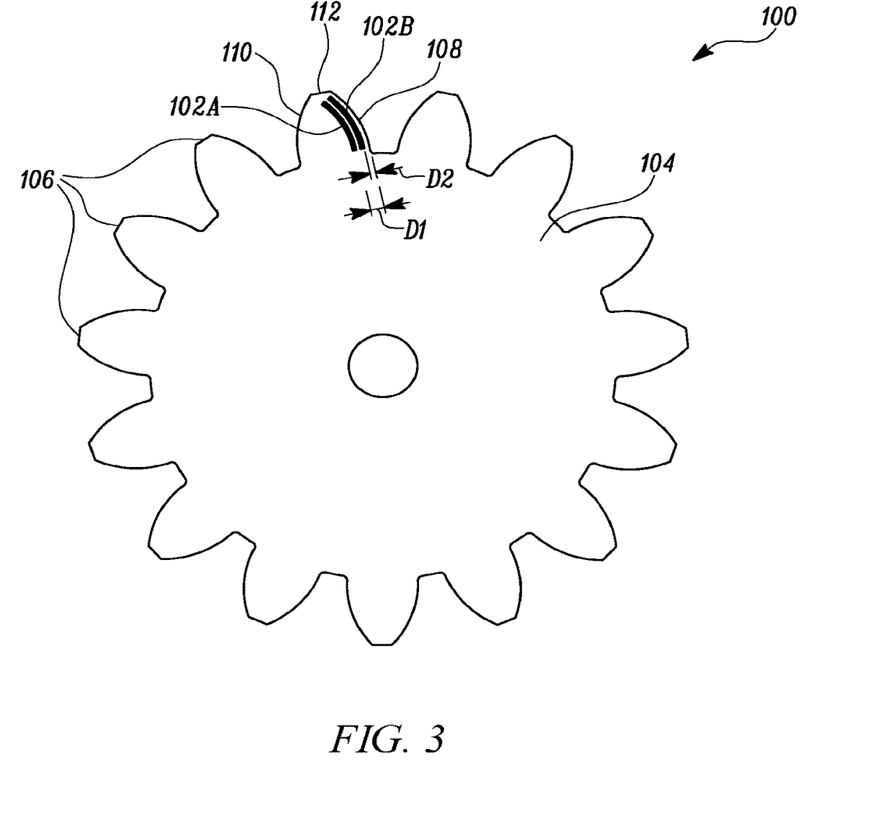
FIG. 3 is a diagrammatic cross-sectional view of a component with wear-identifying material, according to one or more embodiments of the present disclosure.

FIG. 3 illustrates a diagrammatic cross-sectional view of the metal gear component 100 with the wear-identifying material 102, according to one or more embodiments of the present disclosure. The metal gear component 100 may include the wear identifying material 102 embedded in the metal body 104 in the form of a first wear-identifying layer 102A and at least one second three-dimensional printed wear-identifying layer 102B. The at least one second three-dimensional printed wear-identifying layer 102B is hereinafter referred to as the second wear-identifying layer 102B. The characteristics and positioning of the first wear-identifying layer 102A may be similar to or the same as the first wear-identifying layer 102 as explained in relation to FIG. 1.

The second wear-identifying layer 102B can be embedded in the tooth 106 of the metal body 104 at a second predetermined depth 'D2' from the first outer surface portion 108. The second wear-identifying layer 102B may be disposed in such a manner that the second wear-identifying layer 102B is surrounded by the metal body 104, either fully or partially. Therefore, the second wear-identifying layer 102B may or may not be exposed to the atmosphere when embedded in the metal body 104. Further, the second wear-identifying layer 102B may be disposed between the first outer surface portion 108 and the first wear-identifying layer 102A. Therefore, in such a situation, the second predetermined depth D2 of the second wear-identifying layer 102B is less than the first predetermined depth D1 of the first wear-identifying layer 102A.

Figure 4:
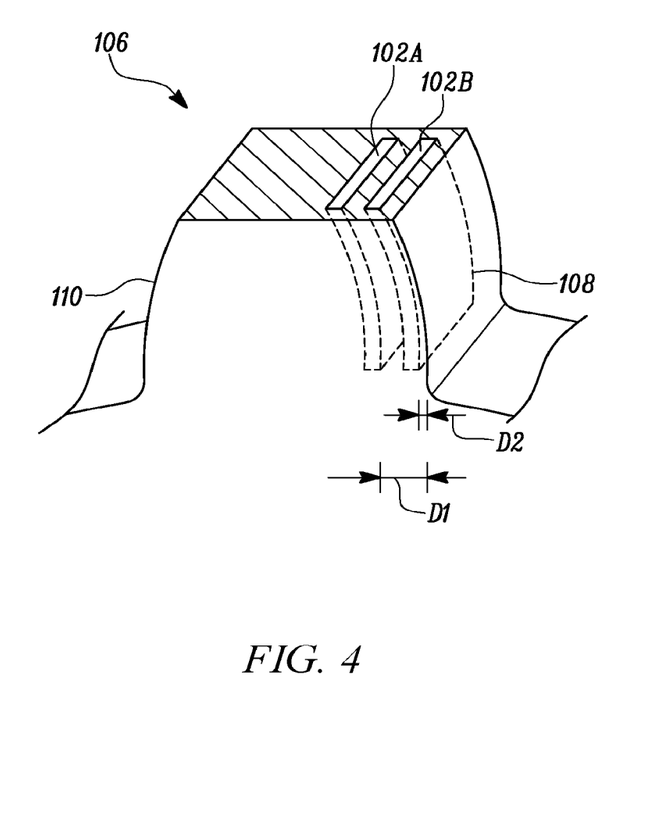
FIG. 4 is a diagrammatic cut-away view of a top surface portion of a tooth of the component of FIG. 3.

To provide a better understanding of the positioning of the first wear-identifying layer 102A and the second wear-identifying layer 102B in the metal body 104, FIG. 4 illustrates a diagrammatic cut-away view of the top surface portion 112 of the tooth 106 of the metal gear component 100.

The second wear-identifying layer 102B can be made of a material, such as metal, different from the first metal of the metal body 104 and the material of the first wear-identifying layer 102A. The material of the second wear-identifying layer may be bronze, chrome, titanium, or a combination of two or more of the foregoing, for instance. In one or more embodiments, the second wear-identifying layer 102B may be formed of a relatively hard non-metal, e.g., carbon fibers.

Further, the material of the second wear-identifying layer may be different from any material used in the oil system, as discussed above relative to FIG. 1.

The first wear-identifying layer 102A and the second wear-identifying layer 102B may be positioned in the metal body 104 so as to detect different wear states of the metal gear component 100. For example, the second wear-identifying layer 102B may indicate wear to a service half-life of the tooth 106 (or outer surface portion) or the metal gear component 100, whereas the first wear-identifying layer 102A may indicate wear to a full service life of the tooth 106 (or outer surface portion) or the metal gear component 100. Therefore, detection of the material of the second wear-identifying layer 102B in an oil sample analysis may indicate wear to the service half-life of the metal gear component 100. Similarly, detection of the material of the first wear-identifying layer 102A in the oil sample analysis may indicate wear to full service life of the metal gear component 100.

Figure 5:
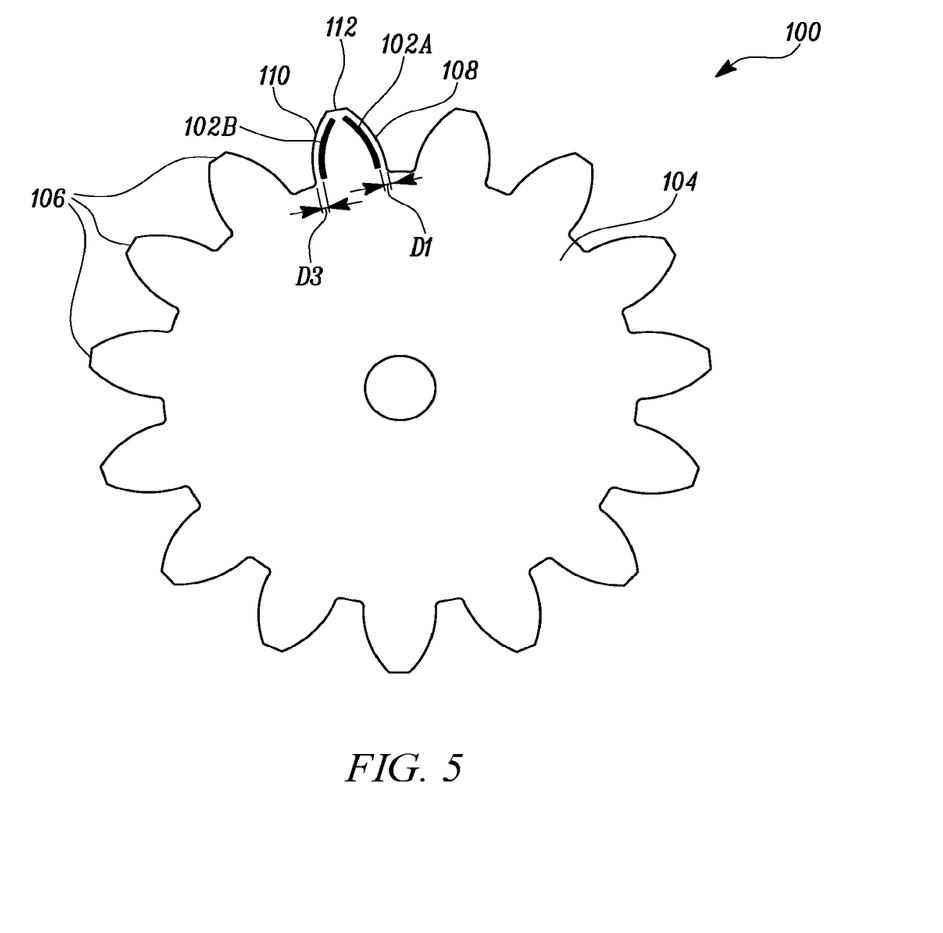
FIG. 5 is a diagrammatic cross-sectional view of a component with wear-identifying material, according to one or more embodiments of the present disclosure.

FIG. 5 illustrates a diagrammatic cross-sectional view of the metal gear component 100 with the wear-identifying material 102, according to one or more embodiments of the present disclosure. The wear-identifying material 102 may include a first wear-identifying layer 102A and a second wear-identifying layer 102B. The characteristics and the positioning of the first wear-identifying layer 102A may be similar to or the same as explained in relation to FIGS. 1, 3, and 4.

The second wear-identifying layer 102B can be embedded in the tooth 106 of the metal gear component 100 at a second predetermined depth 'D3' from the second outer surface portion 110 of the tooth 106. The second outer surface portion 110 is different from the first outer surface portion 108. Since the first wear-identifying layer 102A and the second wear-identifying layer 102B are positioned at two different locations in the metal gear component 100, wear of the metal gear component 100 at different locations may be detected based on detection of loose portions of at least one of the first wear-identifying layer 102A and the second wear-identifying layer 102B in an oil sample analysis. The first predetermined depth D1 may be substantially equal to the second predetermined depth D3. Alternatively, the first predetermined depth D1 may be different from the second predetermined depth D3, for instance, because of different wear rates of the respective surface portions due to a primary movement direction of the metal gear component 100.

Figure 6:
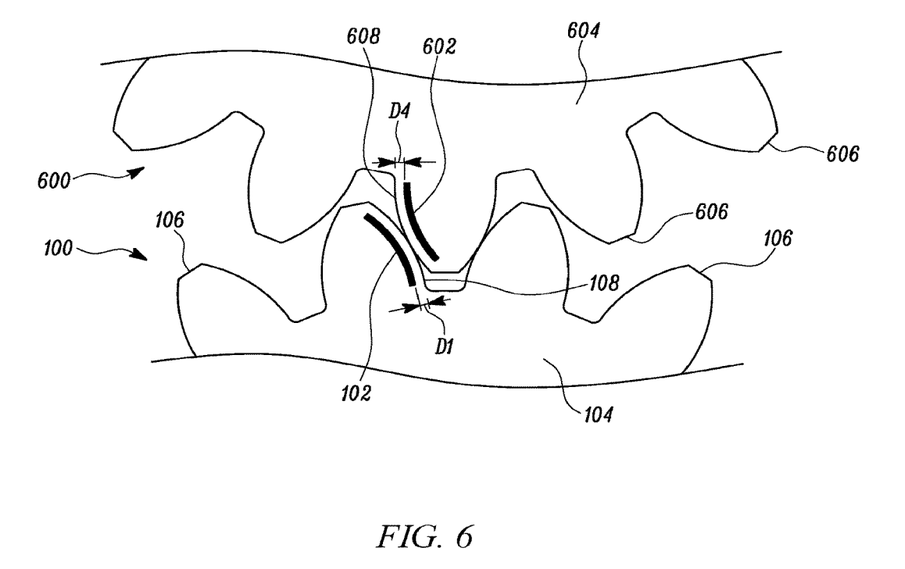
FIG. 6 is a diagrammatic partial cross-sectional view of a component engaged with another component, according to one or more embodiments of the present disclosure.

FIG. 6 illustrates a diagrammatic partial cross-sectional view of the metal gear component 100 in engagement with a second metal gear component 600, according to one or more embodiments of the present disclosure. In one example, the metal gear component 100 and the second metal gear component 600 may be part of a rack and a pinion, respectively.

The metal gear component 100 of FIG. 6 may include the first wear-identifying layer 102 embedded in the metal body 104 at the first predetermined depth D1 from the first outer surface portion 108 of the tooth 106 as explained in relation to FIGS. 1, 3, and 5, for instance. Of course, the metal gear component 100 may have more than one wear identifying layer, such as described above.

The second metal gear component 600 can include a second wear-identifying layer 602 embedded in a metal body 604 including a plurality of teeth 606. The metal body 604 can be made of the first metal, i.e., the same metal from which the metal body 104 is made, or the metal body 604 can be made of a metal different from the metal from which the metal body 104 is made. Further, the second wear-identifying layer 602 can be embedded in at least one tooth 606 at a second predetermined depth 'D4' from a first outer surface portion 608 of the tooth 606. The characteristics of the second wear-identifying layer 602 may be similar to or the same as the wear-identifying layers discussed above with respect to FIGS. 1-5. For example, the second wear-identifying layer 602 may be made of the same material as the second wear-identifying layer 102B discussed above, which can be different from the first metal of the metal body 104, 604 and the material of the first wear-identifying layer 102.

The presence of loose portions of the material of the wear-identifying layer 102 in an oil sample analysis may indicate a wear state or amount of wear of the metal gear component 100. Similarly, the presence loose portions of the material of the second wear-identifying layer 602 in the oil sample analysis may indicate a wear state or amount of wear of the second metal gear component 600. Therefore, different wear-identifying material can be embedded in different metal gear components 100, 600 to uniquely identify wear of different metal gear component 100, 600.

FIG. 7 illustrates a block diagram of a system 700 having a first lubricated sub-system 702, according to one or more embodiments of the present disclosure. The system 700 includes a first three-dimensional printed metal part 704, hereinafter referred to as the first metal part 704, for the first lubricated sub-system 702. In one or more embodiments, the characteristics and operational features of the first lubricated sub-system 702 and the first metal part 704 may be similar to or the same as the oil system and metal gear component 100 as explained relative to FIGS. 1, 2, 3, 4, 5, and 6, for instance. Therefore, the metal gear component 100 can be the first metal part 704. For the sake of brevity, the details of the first lubricated sub-system 702 and the first metal part 704 are not explained in detail for the description of FIGS. 7, 8, and 9.

The first metal part 704 may include a first three-dimensional printed metal body and at least one first three-dimensional printed marker layer positioned in the first three-dimensional printed metal body. The first three-dimensional printed metal body and the at least one first three-dimensional printed marker layer are hereinafter referred to as the first metal body and the first marker layer, respectively.

The first metal body may be formed of a plurality of metal layers of a first metal. The first metal body may include a plurality of contact surfaces. Further, the first marker layer may be made of a first material, which may be different from the first metal. In one or more embodiments of the present disclosure, the first material may be a metal, such as a metal not found or typically found in the first lubricated sub-system 702. The first marker layer may be positioned in the first metal body at a first predetermined depth from a first contact surface of the plurality of contact surfaces. The first predetermined depth may be set or defined so as to indicate an amount of wear of the first contact surface. The amount of wear of the first contact surface may be associated with replacement of the first metal part, including either present or anticipated replacement of the first metal part.

The system 700 can also include a lubricant analysis sensor or sensor circuitry 706 in communication with the first lubricated sub-system 702. The lubricant analysis sensor circuitry 706 can detect loose portions of the first marker layer in lubricant of the first lubricated sub-system 702. That is, when wear of the first metal part reaches the first marker layer and the first marker layer begins to wear, particles of the first marker layer, also referred to as the loose portions, may be introduced into the lubricant of the first lubricated sub-system 702. Such loose portions may be detected by the lubricant analysis sensor circuitry 706 during an oil sample analysis, for instance, performed at or onboard the system 700. The loose portions of the first marker layer may affect a dielectric constant of the lubricant of the first lubricated sub-system 702. In such a case, the lubricant analysis sensor circuitry 706 can detect a change in the dielectric constant of the lubricant to indicative of the existence of the loose portions and thus a corresponding wear state of the first metal part and/or first contact surface of the first metal part.

FIG. 8 illustrates a block diagram of a system 800 having a first lubricated sub-system 802, according to one or more embodiments of the present disclosure. According to FIG. 8, the system 800 may include a second three-dimensional printed metal part 804, hereinafter referred to as the second metal part 804, for the first lubricated sub-system 802. Therefore, the first lubricated sub-system 802 may include the first metal part 704 and the second metal part 804. The characteristics and operational features of the first metal part 704 and the second metal part 804 may be similar to or the same as the metal gear component 100 and the second metal gear component 600 as explained above relative to FIG. 6, for instance.

The second metal part 804 may include a second three-dimensional printed metal body and at least one second three-dimensional printed marker layer positioned in the second three-dimensional printed metal body. The second three-dimensional printed metal body and the at least one second three-dimensional printed marker layer are hereinafter referred to as the second metal body and the second marker layer, respectively. The second metal body may include a plurality of contact surfaces.

The second marker layer may be positioned in the second metal body at a second predetermined depth from a second contact surface of the plurality of contact surfaces of the second metal body. The second predetermined depth may be set or defined so as to indicate an amount of wear of the second contact surface, which may be associated with a current or anticipated replacement of the second metal part 804. Further, the second marker layer may be made of a second material that is different from the first metal of the first metal body and the first material of the first marker layer of the first metal part 704. In another embodiment, the second marker layer can be made of the first material.

The system 800 can include a lubricant analysis sensor or sensor circuitry 806 in communication with the first lubricated sub-system 802. The lubricant analysis sensor circuitry 806 can detect existence of loose portions of the first marker layer and loose portions of the second marker layer in the lubricant of the first lubricated sub-system 802. The sensor circuitry 806 and/or a corresponding processor or processing circuitry (which can be part of the sensor circuitry or vice versa) can analyze sensed or detected characteristics of the lubricant to identify which of the first and second marker layer portions exist in the lubricant. Such analysis and information can be used to identify a wear state or amount of a corresponding printed metal body. Wear information may be electronically transmitted from the sensor circuitry 806 and/or processing circuitry to be output on a control panel or display. Such information can be transmitted via wired or wireless communication mediums, and the control panel or display can be part of the system 800 or remote from the system 800.

FIG. 9 illustrates a block diagram of a system 900 in communication with the first lubricated sub-system 702, for instance, according to FIG. 7 and corresponding description, and a second lubricated sub-system 902, according to one or more embodiments of the present disclosure.

The system 900 can include the first metal part 704 for the first lubricated sub-system 702, and the second metal part 804 for the second lubricated sub-system 902. For the sake of brevity, the first metal part 704 and the second metal part 804 are not explained in detail in the description for FIG. 9, and the corresponding details can be referred to from the description above, such as relative to FIG. 7 and FIG. 8.

The system 900 can include a first lubricant analysis sensor or sensing circuitry 904, a second lubricant analysis sensor or sensing circuitry 906, and a processor or processing circuitry 908. The first lubricant analysis sensor 904 can detect loose portions of the first marker layer in the lubricant of the first lubricated sub-system 702, in case of wear of the first marker layer of the first metal part 704. The second lubricant analysis sensor 906 can detect loose portions of the second marker layer in the lubricant of the second lubricated sub-system 902, in case of wear of the second marker layer of the second metal part 804. The processor 908 can identify respective wear states of the first metal part 704 and the second metal part 804. Further, the processor 908 may identify the wear states based on the detection by the first lubricant analysis sensor 904 and the second lubricant analysis sensor 906.

INDUSTRIAL APPLICABILITY

The present disclosure relates to a component 100, 600, 704, 804, particularly that is or has been additive manufactured (including 3-D printed), with a wear-identifying material 102, which has also been additive manufactured into the component. The present disclosure also relates to a system 700, 800, 900 and a method 1000 for detection of wear in the component 100, 600, 704, 804.

The present disclosure is applicable to any component that is prone to wear over a period of time, though the present disclosure particularly implements the component in the context of lubricated systems, such as enclosed oil systems. The wear-identifying material 102 may be embedded in the component 100, 600, 704, 804 in any form or shape, and at any position. In various embodiments, the wear-identifying material 102 is embedded in the form of layers 102, 102A, 102B, 602. Wear of the component 100, 600, 704, 804 may be detected by detection of loose portions of the wear-identifying material 102 in the lubricant during an oil sample analysis, for instance.

Although the present disclosure is explained with regard to a metal gear component 100, 600, the first metal part 704 and the second metal part 804, the scope of the present disclosure is not limited to the components 100 explained in the disclosure. Further, the present disclosure may include detection of wear in any component, without departing from the scope of the disclosure.

Figure 10:
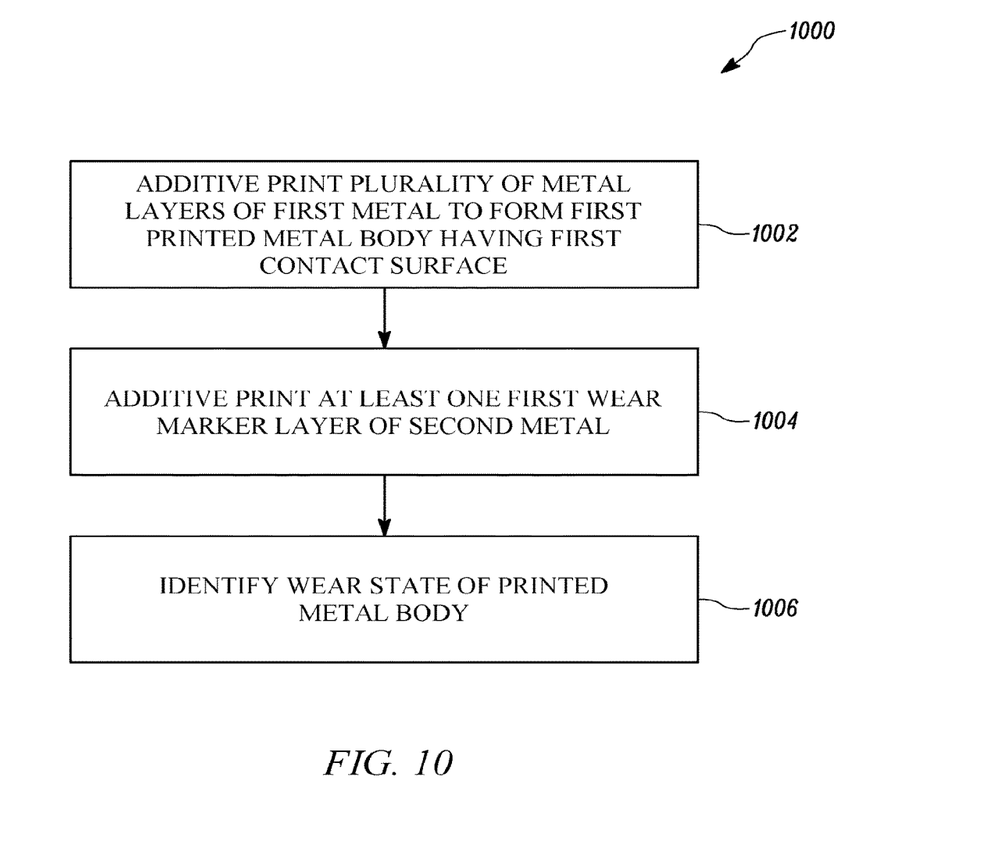
FIG. 10 is a flowchart for a method of indicating wear of a component, according to one or more embodiments of the present disclosure.

FIG. 10 illustrates a flowchart for a method 1000 of indicating wear of a component, such as the metal gear component 100, the second metal gear component 600, the first metal part 704, and the second metal part 804, according to one or more embodiments of the present disclosure.

At step 1002, the method 1000 includes additive printing a plurality of metal layers of a first metal to form a first printed metal body. The characteristics and operational features of the first printed metal body may be similar to or the same as the metal body 104, 604 as explained relative to FIGS. 1, 2, 3, 4, 5, and 6, respectively, for instance. The first printed metal body may include a first contact surface. To be clear, step 1002 can form part of the printed metal body, since, as discussed below, a wear marker layer is additive printed into the printed metal body so as to be embedded, partially or fully.

At step 1004, the method 1000 includes additive printing at least one first printed wear marker layer of a material different from the material of the printed body. The characteristics and operational features of the first printed wear marker layer may be similar to the first wear-identifying layer 102 and the first marker layer as explained in the embodiments of FIGS. 1, 2, 3, 4, 5, 6, 7, 8, and 9, respectively, for instance. Further, step 1004 can include additive printing of the first metal to fully or partially enclose the first marker layer and thus finish the first printed metal body (i.e., at least the additive manufacturing operations). Further steps, such as applying a coating layer to the first printed metal body, may be performed as part of step 1004 or after step 1004.

As noted above, a first printed wear marker layer may be provided in the first printed metal body at the first predetermined distance D1 away from a first contact surface. The first predetermined distance can represent an amount of wear of the first contact surface associated with the replacement of the first printed metal body.

In one or more embodiments, the method 1000 can further include a step S1006 of sensing existence of free portions of the first wear marker layer in the lubricant of the lubricated systems 702, 802, 902 in which the first printed metal body is provided. The sensing may be performed external to a machine comprising the lubricated system 802, 902, or it may be performed by onboard sensing circuitry (which can include a processor or processing circuitry or vice versa).

In another embodiment, the method 1000 includes additive printing at least one second wear marker layer, for instance, prior to completing the first printed metal body. The second wear marker layer may also be provided in the first printed metal body. The characteristics and operational features of the second printed wear marker layer may be similar to or the same as the second wear-identifying layer 102B, 602 and the second marker layer as explained relative to FIGS. 1, 2, 3, 4, 5, 6, 7, 8, and 9, respectively, for instance.

Optionally, the method 1000 can include additive printing at least one second wear marker layer of a material such as a third metal. The third metal may be different from the second metal. In one or more embodiments, the third metal may be different from the first metal. The second printed wear marker layer may be provided in the first printed metal body at a second predetermined distance away from the first contact surface. Additionally or alternatively, the printed second wear marker layer may be provided in the first printed metal body at the second predetermined distance away from a second contact surface.

As noted above, in one or more embodiments, the method 1000 can optionally include a step 1006 of determining a wear state of the first printed metal body based on detection of existence of loose particles of the first wear marker layer.

Further, in one or more embodiments, the method 1000 includes additive printing a plurality of metal layers of the first metal to form a second printed metal body having a second contact surface. The method 1000 can further include additive printing at least one second wear marker layer, for instance, of a third metal different from the first metal and the second metal. The printed second wear marker layer may be provided in the second printed metal body at a second predetermined distance away from the second contact surface.

The method 1000 can further include in step 1006, sensing existence of the loose portions of one or more of the first wear marker layer and the second wear marker layer in lubricant of a lubricated system 802, 902 in which the first printed metal body and the second printed metal body are provided. The sensing may be performed external to the machine including the first and second lubricated system 802, 902. Additionally or alternatively, the sensing may be performed onboard the machine.

The component 100, 600, 704, 804, the system 700, 800, 900, and the method 1000 of the present disclosure, or portions thereof, can result in timely wear detection, in some cases automatically, and without the need to open an enclosed oil system. The detection of the wear-identifying material 102 in the lubricant during the oil sampling analysis can eliminate the need of a visual inspection of the component 100, 600, 704, 804 for wear. Further, the oil sample analysis can be done onboard as well off-board the machine, thereby providing flexibility in wear detection.

The wear-identifying material 102 may be selectively embedded or positioned in the component 100, 600, 704, 804 based on expected wear of different portions of the component 100, 600, 704, 804. For example, the wear-identifying material 102 may be positioned in different portions of the component 100, 600, 704, 804 at different depths from an outer surface. Further, various wear states, such as service half-life and full service life, of a portion of the component 100, 600, 704, 804 may be determined by placing multiple layers of different wear-identifying material 102 in succession, either directly after one another or in spaced apart relation from one another. Similarly, different wear-identifying material 102 may be embedded in different portions of the component 100, 600, 704, 804, or may be in different components 100, 600, 704, 804, to determine a wear state or amount of different portions or components 100, 600, 704, 804. Such analysis can also assist in designing components 100, 600, 704, 804 based on a trend and rate of wear detected in various portions of the components 100, 600, 704, 804.

Further, wear-identifying material 102 may be embedded in the components 100, 600, 704, 804 of different lubricated systems 702, 802 to detect wear in the different lubricated system 702, 802, for instance, concurrently. Additionally, wear detection can be automated by the inclusion of lubricant sensor circuitry and/or processing circuitry (which may be part of the sensor circuitry or vice versa).

While aspects of the present disclosure have been particularly shown and described with reference to the embodiments above, it will be understood by those skilled in the art that various additional embodiments may be contemplated by the modification of the disclosed machines, systems and methods without departing from the spirit and scope of what is disclosed. Such embodiments should be understood to fall within the scope of the present disclosure as determined based upon the claims and any equivalents thereof.

What is claimed is:

1. A system comprising:
   a first three-dimensional printed metal part for a first lubricated sub-system, the first three-dimensional printed metal part including:
      a first three-dimensional printed metal body formed of a plurality of metal layers of a first metal and having a plurality of contact surfaces,
      at least one first three-dimensional printed marker layer of a first material different from the first metal, positioned in the first three-dimensional printed metal body at a first predetermined depth from a first contact surface of the plurality of contact surfaces,
   wherein the first predetermined depth is indicative of an amount of wear of the first contact surface associated with replacement of the first three-dimensional printed metal part, and
   lubricant analysis sensor circuitry configured to perform an on-board detection of loose portions of the at least one first three-dimensional printed marker layer in lubricant of the first lubricated sub-system where the lubricant and the first three-dimensional printed metal part remain in the first lubricated sub-system and the first lubricated sub-system remains closed.

2. The system of claim 1, further comprising a second three-dimensional printed metal part for the first lubricated sub-system, the second three-dimensional printed metal part including:
   a second three-dimensional printed metal body having a plurality of contact surfaces, and
   at least one second three-dimensional printed marker layer positioned in the second three-dimensional printed metal body at a second predetermined depth from a second contact surface of the plurality of contact surfaces of the second three-dimensional printed metal body, the second predetermined depth being indicative of an amount of wear of the second contact surface associated with replacement of the second three-dimensional printed metal part.

3. The system of claim 2, wherein the at least one second three-dimensional printed marker layer is comprised of a second material different from the first material and the first metal, the first material of the at least one first three-dimensional printed marker layer and the second material of the at least one second three-dimensional printed marker layer being different materials from any other material inside the first lubricated sub-system.

4. The system of claim 2, further comprising lubricant analysis sensor circuitry configured to detect existence of loose portions of the at least one first three-dimensional printed marker layer and existence of loose portions of the at least one second three-dimensional printed marker layer in lubricant of the first lubricated sub-system, the loose portions of the at least one first three-dimensional printed marker layer and the loose portions of the at least one second three-dimensional layer each having a constitution that affects a dielectric constant of the lubricant of the first lubricated sub-system.

5. The system of claim 1, further comprising a second three-dimensional printed metal part for a second lubricated sub-system, the second three-dimensional printed metal part including:
   a second three-dimensional printed metal body having a plurality of contact surfaces, and
   at least one second three-dimensional printed marker layer positioned in the second three-dimensional printed metal body at a second predetermined depth from a second contact surface of the plurality of contact surfaces of the second three-dimensional printed metal body, the second predetermined depth being indicative of an amount of wear of the second contact surface associated with replacement of the second three-dimensional printed metal part.

6. The system of claim 5, wherein the lubricant analysis sensor circuitry includes:
   a first lubricant analysis sensor configured to detect loose portions of the at least one first three-dimensional printed first marker layer in lubricant of the first lubricated sub-system;

a second lubricant analysis sensor configured to detect loose portions of the at least one second three-dimensional printed marker layer in lubricant of the second lubricated sub-system; and a processor configured to identify wear states of the first three-dimensional printed metal part and the second three-dimensional printed metal part based on signals from the first and second lubricant analysis sensors.

7. The system of claim 1, further comprising at least one second three-dimensional printed marker layer of a second material different from the first metal and the first material, positioned in the first three-dimensional printed metal body at a second predetermined depth from the first contact surface of the plurality of contact surfaces, the first and second three-dimensional printed marker layers being representative of different wear states of the first three-dimensional printed metal part.

8. The system of claim 1, further comprising at least one second three-dimensional printed marker layer of a second material different from the first metal and the first material, positioned in the first three-dimensional printed metal body at the first predetermined depth from a second contact surface of the plurality of contact surfaces, the first and second three-dimensional printed marker layers being representative of different wear states of different surfaces of the first three-dimensional printed metal part.

9. A method comprising:
additive printing a plurality of metal layers of a first metal to form a first printed metal body having a first contact surface;

additive printing at least one first wear marker layer of a second metal, different from the first metal, the at least one first wear marker layer being provided in the first printed metal body at a first predetermined distance away from the first contact surface, wherein the first predetermined distance is indicative of an amount of wear of the first contact surface associated with replacement of the first printed metal body, providing a lubricant analysis sensor circuitry configured to detect loose portions of the at least one first three-dimensional printed marker layer in lubricant of the first lubricated sub-system; and performing, using the lubricant analysis sensor circuitry, an on-board detection of the loose portions of the at least one first three-dimensional printed marker layer in the lubricant of the first lubricated sub-system when the lubricant and the first three-dimensional printed metal part remain in the first lubricant sub-system and the first lubricated sub-system remains closed.

10. The method of claim 9, further comprising determining a wear state of the first printed metal body based when said detection of loose portions indicates existence of free portions of the at least one wear marker layer.

11. The method of claim 9, further comprising additive printing at least one second wear marker layer of the second metal, the at least one second wear marker layer being provided in the first printed metal body and spaced apart from the at least one first wear marker layer.

12. The method of claim 9, further comprising additive printing at least one second wear marker layer of a third metal, different from the second metal, the at least one second wear marker layer being provided in the first printed metal body at a second predetermined distance away from the first contact surface.

13. The method of claim 9, further comprising additive printing at least one second wear marker layer of a third metal, different from the second metal, the at least one second wear marker layer being provided in the first printed metal body at a second predetermined distance away from a second contact surface of the first printed metal body.

14. The method of claim 9, further comprising:
additive printing a plurality of metal layers of the first metal to form a second printed metal body having a second contact surface; and additive printing at least one second wear marker layer of a third metal, different from the first metal and the second metal, the at least one printed second wear marker layer being provided in the second printed metal body at a second predetermined distance away from the second contact surface of the second printed metal body.

15. The method of claim 9, wherein at least one second three-dimensional printed marker layer of a second material different from the first metal and the first material is positioned in the first three-dimensional printed metal body at a second predetermined depth from the first contact surface of the plurality of contact surfaces, the first and second three-dimensional printed marker layers being representative of different wear states of the first three-dimensional printed metal part.

16. The method of claim 9, wherein at least one second three-dimensional printed marker layer of a second material different from the first metal and the first material is positioned in the first three-dimensional printed metal body at the first predetermined depth from a second contact surface of the plurality of contact surfaces, the first and second three-dimensional printed marker layers being representative of different wear states of different surfaces of the first three-dimensional printed metal part.

\* \* \* \* \*